United States Patent [19]
Langberg

[11] Patent Number: 5,248,312
[45] Date of Patent: Sep. 28, 1993

[54] LIQUID METAL-FILLED BALLOON

[75] Inventor: Edwin Langberg, Mt. Laurel, N.J.

[73] Assignee: Sensor Electronics, Inc., Mt. Laurel, N.J.

[21] Appl. No.: 891,802

[22] Filed: Jun. 1, 1992

[51] Int. Cl.⁵ ............................................. A61B 17/36
[52] U.S. Cl. ............................................. 606/28; 606/27; 607/113
[58] Field of Search .................. 128/401, 402, 403; 604/96; 606/192, 33, 27, 28, 29

[56] References Cited
U.S. PATENT DOCUMENTS 4,949,718  8/1990  Neuwirth et al. ............ 606/27 X
4,979,518 12/1990  Itoh et al. .................... 606/28 X
5,006,119  4/1991  Acker et al. ................. 606/28 X
5,084,044  1/1992  Quint .......................... 128/401
5,151,100  9/1992  Abele et al. .................. 606/28

Primary Examiner—Peter A. Aschenbrenner

[57] ABSTRACT

Liquid metal gallium-filled balloon catheter is connected to a source of heating power. An improved method of hyperthermia and ablation is made possible by ease of insertion and conformity to complex intracavitary geometry by liquid metal. Closeness of gallium melting point to body temperature makes insertion of solid gallium possible and subsequent melting after insertion. Method of balloon ablation of endometrium is described.

6 Claims, 1 Drawing Sheet

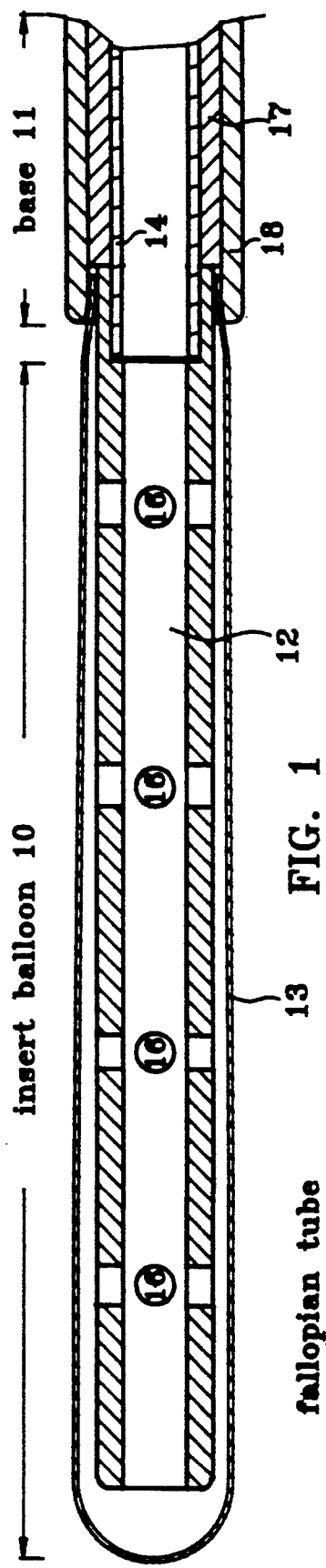
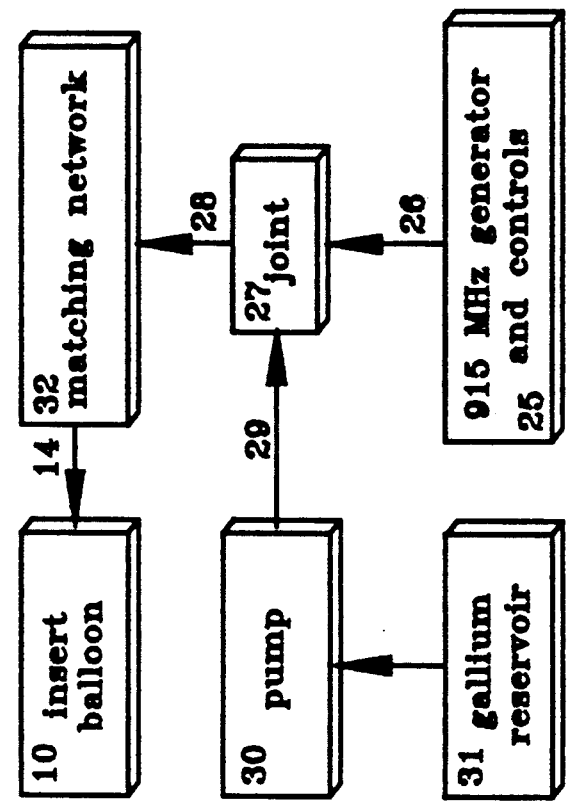
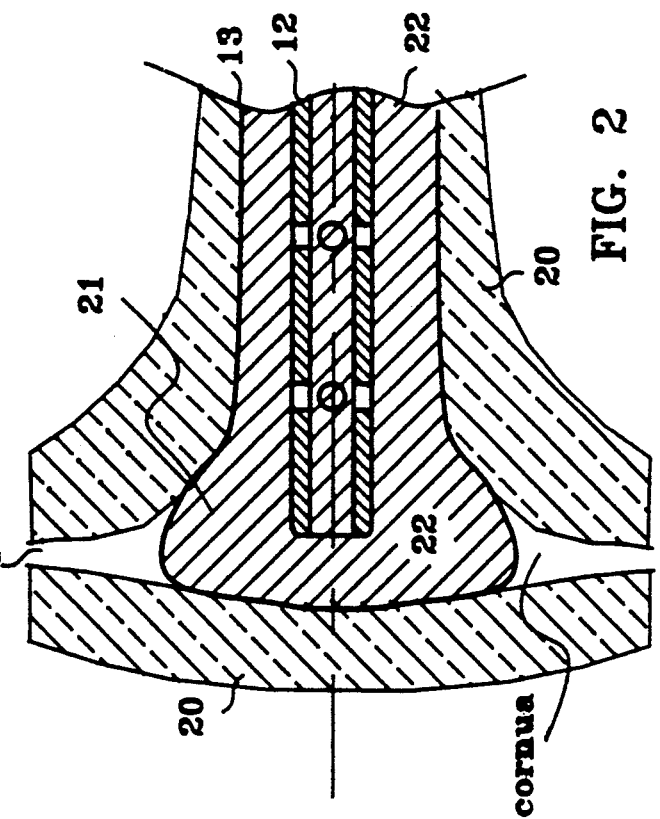

LIQUID METAL-FILLED BALLOON

BACKGROUND OF THE INVENTION

1. Field of the Invention

The present invention relates to liquid metal-filled balloon catheters suitable for application in hyperthermia and ablation, and specifically to the method of use of balloon catheters in endometrial ablation.

2. Related Art

Medical electrical heating catheters are used for tissue heating, typically in oncological hyperthermia (e.g., Chou et al., U.S. Pat. No. 4,865,047), in prostatic hyperplasis (e.g., Turner el al., U.S. Pat. No. 4,967,765) and also in thermal ablation of tissue exemplified by destruction of cardiac arrhythmogenic tissue (e.g., Langberg, U.S. Pat. No. 4,945,912). Electrical heating is accomplished by applying electrical power through a metal electrode equipped applicator to tissue. A wide variety of styles of electrodes for applicators exists, adapted to the geometry of the tissue to be heated and to the frequency of the applied electrical field which can range from DC pulses to microwaves. Generically, heating by Electro-Magnetic Radiation (EMR) is characterized by providing a metallic electrode serving as a conductor to guide the penetration of the EMR field into the tissue.

Typically, EMR applicators have rigid metallic electrodes, which are adequate for many applications but not when the geometry of the organ to be heated is complex, or the geometry of the organ varies greatly from patient to patient, or the organ exhibits plasticity requiring application of a very uniform pressure during the procedure. The required size of the rigid electrode may also cause difficulty when inserting the device. Geddes et al. in U.S. Pat. No. 4,979,948 proposes a radio-frequency (RF) ablation catheter using an liquid electrolyte-filled balloon, which overcomes the inconvenience of a rigid electrode. The current-emitting electrode of Geddes heats primarily the electrolyte inside the balloon because the conductivity and the dielectric constant of tissue is typically of the same order of magnitude as an electrolyte solution. Heating of the tissue is done primarily by heat conduction from a hot balloon which could be accomplished by an ordinary heater. The objective of the RF heating is to let the RF field in the tissue do the heating which requires much higher conductivity of the fluid in the balloon.

A principal feature distinguishing the present invention from prior art devices is the use of a liquid metal, and specifically, a gallium-filled balloon to serve as an applicator of an electrode catheter. The liquid metal-filled balloon applicator has the advantages of fluidity and so is inherently capable of a small cross section for easy insertion and subsequent expansion in conformity to a complex and variable geometry of intracavitary space. Metallic conductivity prevents any electric fields to form inside liquid metal-filled balloon and forces electric fields to the surface where they interact with the tissue.

EMR heating catheters with rigid applicators are used for endometrial ablation of the uterus, as reported by Phipps et al. in *Obstetrics & Gynecology*. Vol. 76, No. 5, Part 1, November: 876-881, 1990 and also in European Patent Application No. 0 407 057 A1 by Stanley B. Field and Jeffrey H. Phipps ("Phipps et al"). This catheter is much simpler to use than the hysteroscopic techniques now frequently employed for endometrial ablation. Phipps et al reports use of a straight and a curved applicator probe. The disadvantage of the straight probe applicator, as reported by Phipps et al, is that because of the shape of the uterus (see FIG. 2) the cornua is not exposed to adequate electric field heating, leading to incomplete endometrial ablation in the cornua region. A curved probe tip which fits into the cornua requires 360 degree rotation during the procedure. The curvature of the tip is quite critical and there is delicate compromise between good apposition of the cornua and safety concerns relating to intrauterine injury due to the required rotation of the curved probe.

Another feature of the present invention is the application of balloon method for performance of endometrial ablation.

SUMMARY OF THE INVENTION

Accordingly, the principal object of the present invention is utilization of liquid metals, particularly gallium, as a flexible, injectable, electrical and heat-conducting electrode material and balloon expansion fluid, and the method of use of the same for medical procedures. Liquid metal, injected directly or as a filling fluid of a balloon, has a natural tendency to fill anatomical intracavitary space and to maintain an intimate contact with the cavity wall, regardless of wall irregularity, patient-to-patient variability, or movement of the organ wall. The liquid metal applicator geometry and exerted pressure can be modified during the procedure, e.g., by applying pressure to cause expansion. Due to its metallic properties, the liquid metal applicator maintains electrical and thermal conduction typical of metals.

There are two metals which are liquid at body temperature: mercury and gallium. Mercury is a more common element of the two, but its toxicity limits its applications. Gallium with its low toxicity is well suited to the task. Gallium can be readily frozen into a solid shape for the task of insertion and then melted when exposed to body heat.

A specific object of the present invention is to provide an apparatus using a gallium-filled balloon for electromagnetic heating with or without concomitant expansion. Such a balloon can be connected, or alternatively, can be externally coupled to a generator of electromagnetic energy. Gallium can be injected or withdrawn from the balloon thereby controlling size of the balloon and wall pressure exerted by the balloon. Applications include, but are not limited to endometrial ablation, cardiac ablation, and benign prostatic hypertrophy. Advantage of the present invention is that liquid metal-filled devices maintain flexibility, injectability and conformity to complex shapes, absent in solid metal elements, while possessing the electrical and thermal conductive properties typical of all metals.

Another object of the present invention is a gallium applicator which is frozen in a solid shape at the beginning of the procedure and when in place melts into a pliable liquid applicator as a result of the exposure to body heat.

Yet another object of this invention is the method of performance of endometrial ablation using a flexible balloon.

BRIEF DESCRIPTION OF THE DRAWINGS

Other objects and features of this invention will become more readily apparent from the following detailed description when read in conjunction with the accompanying drawings, in which:

FIG. 1 is a cross-section view of a balloon applicator ready for gallium filling;

FIG. 2 shows a gallium-filled balloon inside of a uterus deployed for endometrial ablation and illustrates the method of balloon ablation of the endometrium; and FIG. 3 is a block diagram of the connection of the gallium-filled balloon catheter to a gallium pump and a source of RF power.

DETAILED DESCRIPTION OF THE PREFERRED EMBODIMENT

Referring now to FIG. 1, a gallium-filled balloon applicator comprises insert balloon 10 connected to a base 11. In the chosen preferred embodiment, insert balloon 10 is a gallium-filled balloon used as an EMR heating applicator. In FIG. 1, the insert balloon 10 is not yet filled with gallium in order to better show elements of the applicator. A perforated tube 12 of 3.3 mm outside diameter supports a latex sheath 13 of 5 mil wall thickness. At the base 11, the perforated tube 12 mates with a flow tube 14. The flow tube serves a dual role: it is an electrical conductor of electromagnetic energy and it serves as a conduit for liquid gallium. Connection between flow tube 14 and a matching network 32 is not shown in FIG. 1, but is discussed later in connection with FIG. 3.

In FIG. 2 a distal end of the insert balloon 10 is shown filled with gallium 21 in uterine cavity 22. Liquid gallium 21 is pumped by pump 30 shown in FIG. 3, through a network of tubes (shown by the arrows in FIG. 3) and through the perforated tube 12 into the interior of the latex sheath 13. The pumping action is initiated once the insert balloon 10 is inserted into a uterus 20. The gallium flows through holes 16 in the perforated tube 12 and expands the latex sheath 13 until sheath 13 conforms to uterine cavity 22 in FIG. 2.

An alternative means of insertion of the insert balloon 10 can be accomplished by substituting the perforated tube 12 with a slug of frozen gallium. The melting point of gallium is 30° C. (86° F.) and so gallium can be frozen at ordinary refrigerator temperatures in a mold of the desired shape prior to insertion. Since body temperature is above the melting point of gallium, the solid gallium slug will melt after insertion into uterus 20 and fill the latex sheath 13 to conform to the uterine cavity 22.

During the endometrial ablation procedure, base 11 contacts the cervix and forms a cervical heat shield. In the base 11, flow tube 14 is covered by a coaxial insulator 17 and this assembly is in turn surrounded by a teflon heat-shrink tube 18. The heat-shrink tube 18 seals the latex sheath 13 to the perforated tube 12 at the base end 11, preventing gallium escape. The heat-shrink tube 18 and the insulator 17 reduce the external electromagnetic field at the base 11 so that the resulting tissue heating of the cervix and vagina is much reduced. The outside diameter of the cervix shield is 4 mm allowing an easy insertion into the uterus 20.

A block diagram of the endometrial ablation system is shown in FIG. 3. The art of connection of an electromagnetic power source to heating catheters is known. For example, Sogawa et al. in U.S. Pat. No. 4,662,383 show a connection of a microwave oscillator endotract hyperthermia balloon. For this reason, only a block diagram description of circuits used is given.

A wide range of frequencies can be used to power the liquid metal-filled balloon. The lowest practical frequency of approximately 27 MHz is determined by the capacitive impedance formed by the wall of the balloon. The highest frequency in low microwave region, is determined by the resonance on the balloon as an antenna, when the dimensions of the balloon are of the order of a wavelength.

FIGS. 1 and 2 not only illustrate the apparatus but also provide the salient features of the method of balloon endometrial ablation. The deflated balloon in FIG. 1 is introduced via vagina and cervix into the uterus. When in the uterus, the balloon is inflated and the ablating agent is applied.

In FIG. 3, a microwave generator 25, capable of up to 500 watts of output, is equipped with controls which adjust and monitor forward and reflected power and maintain optimum impedance match with a coaxial line 26. The coaxial line 26 connects the generator 25 to a joint 27 where the hollow center conductor of coax 28 is joined with a tube 29 from pump 30, which pumps the gallium 21 from a reservoir 31 to the insert balloon 10. The joint 27 is in turn connected through the hollow coax line 28, through a matching network 32, and to the insert balloon shown in FIG. 1. Matching networks are well known in the art. For example, a matching network for application in a liquid-cooled hyperthermia applicator is described in U.S. Pat. No. 4,841,990 by Kikuchi et al. The matching network matches the impedance of the insert balloon, as an antenna, to the impedance of the coaxial line 28.

An alternative coupling of power to a gallium-filled uterus is via an extracoporeal link: The generator of 5 kHz ac power is connected to a ferrite core electromagnet applicator placed externally on the skin of the patient above the uterus. The magnetic field generated by the electromagnet applicator penetrates into the uterus, generates eddy currents in the liquid metal which is in the uterus, causing the generation of heat. The hot liquid metal in turn heats adjoining tissue via heat conduction. The extracorporeal coupling of power greatly simplifies the design of the catheter, since now the only electrical conductors required are those leading to a thermistor used to monitor the temperature of the liquid metal. It also much reduces the danger of injury to the cervix and vagina.

Although a single embodiment of this invention directed at endometrial ablation has been described, it will be apparent to a person skilled in the art that various modification to the detail of construction shown and described may be made for purposes of adaptation to other heating and ablation procedures without departing from the scope of the invention.

What is claimed is:

1. An improved balloon catheter of a type inserted into a bodily cavity, the balloon catheter having means for filling and emptying the balloon with a fluid, wherein the improvement comprises fluid which is a liquid metal.

2. An improved balloon catheter in accordance with claim 1 wherein said liquid metal is gallium.

3. An improved balloon catheter in accordance with claim 1 further comprising means for pumping said liquid metal between said balloon and an external reservoir for cooling of the balloon.

4. An improved balloon catheter in accordance with claim 1 wherein said liquid metal, filling said balloon, forms an electrode separated from said bodily cavity by a wall of said balloon, and further comprising a generator of electromagnetic power connected to said electrode for heating of said bodily cavity.

5. An improved balloon catheter in accordance with claim 1 further comprising an external applicator of electromagnetic power for coupling the power to said liquid metal filling the balloon thereby heating said bodily cavity.

6. A method of using a gallium-filled balloon which comprises external cooling and solidifying of gallium for retention of a predetermined shape, insertion of thus shaped balloon into a bodily cavity, followed by melting of gallium by application of heat for conformal filling of a bodily cavity.

* * * * *